United States Patent
Schwenker et al.

(10) Patent No.: US 10,936,398 B2
(45) Date of Patent: Mar. 2, 2021

(54) METHOD OF DYNAMICALLY SAVING METADATA IN A PROCESS OF OPERATING A MEDICAL SYSTEM, MEDICAL SYSTEM AND COMPUTER PROGRAM PRODUCT

(71) Applicant: Roche Diabetes Care, Inc., Indianapolis, IN (US)

(72) Inventors: Kai-Oliver Schwenker, Haßloch (DE); Ulf Koppetsch, Viernheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 110 days.

(21) Appl. No.: 15/903,546

(22) Filed: Feb. 23, 2018

(65) Prior Publication Data
US 2018/0260278 A1 Sep. 13, 2018

(30) Foreign Application Priority Data
Mar. 10, 2017 (EP) ..................................... 17160335

(51) Int. Cl.
*G06F 11/07* (2006.01)
(52) U.S. Cl.
CPC ...... *G06F 11/0778* (2013.01); *G06F 11/0793* (2013.01)
(58) Field of Classification Search
CPC ............. G06F 11/0778; G06F 11/0787; G06F 11/079; G06F 11/3636
USPC .................................................. 714/38.1, 45
See application file for complete search history.

(56) References Cited

U.S. PATENT DOCUMENTS

| | | | | |
|---|---|---|---|---|
| 6,910,160 B2* | 6/2005 | Bajoria | ............... | G06F 11/0712 714/37 |
| 7,168,002 B2* | 1/2007 | Agha | .................. | G06F 11/0712 714/24 |
| 8,473,251 B1 | 6/2013 | Noth et al. | | |
| 8,904,243 B2* | 12/2014 | Loimuneva | ......... | G06F 11/0787 714/38.1 |
| 9,020,987 B1* | 4/2015 | Nanda | ................. | G06F 16/1734 707/821 |

(Continued)

OTHER PUBLICATIONS

Extended European Search Report in related applicaiton 17160335.0 dated Sep. 14, 2017.

*Primary Examiner* — Joseph R Kudirka
(74) *Attorney, Agent, or Firm* — Woodard, Emhardt, Henry, Reeves & Wagner, LLP

(57) ABSTRACT

The present disclosure refers to a method of dynamically saving metadata in a process of operating a medical system, comprising: running a software application for operating a medical device; storing metadata in a transient memory by a controller, wherein the metadata are assigned to one or more operation events while the software application is running; detecting an error operation event by the controller; in response to the detecting the error operation event, transmitting present metadata currently stored in the transient memory and assigned to one or more operation events before the error operation event was detected from the transient memory to a log data memory; storing the present metadata in the log data memory; and storing metadata different from the present metadata and assigned to the error operation event in the log data memory. Further, a medical system, and a computer program product are provided.

11 Claims, 2 Drawing Sheets

(56) References Cited

U.S. PATENT DOCUMENTS

Figure 1:
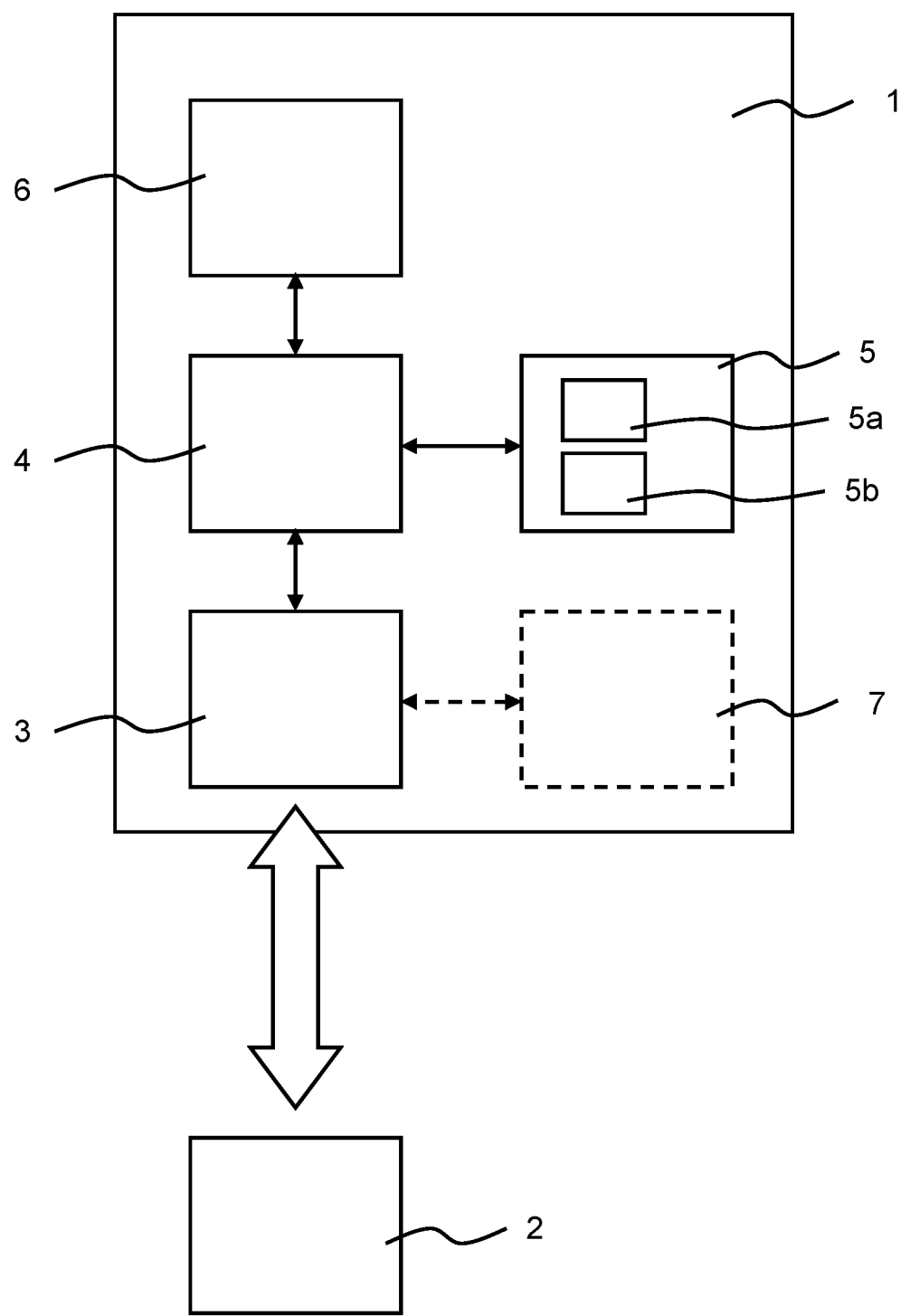

| | | | |
|---|---|---|---|
| 9,442,791 B2* | 9/2016 | Bello | G06F 11/0778 |
| 2009/0077420 A1 | 3/2009 | Sunavala et al. | |
| 2013/0055032 A1 | 2/2013 | Cole et al. | |
| 2016/0094620 A1* | 3/2016 | Darling | H04L 67/10 709/204 |

* cited by examiner

METHOD OF DYNAMICALLY SAVING METADATA IN A PROCESS OF OPERATING A MEDICAL SYSTEM, MEDICAL SYSTEM AND COMPUTER PROGRAM PRODUCT

The present disclosure refers to a method of dynamically saving metadata in a process of operating a medical system, a medical system, and a computer program product.

BACKGROUND

Medical systems may be operated by running one or more software applications controlling functionalities or operation of the medical system, specifically a medical device which is provided with the medical system. For example, the medical device may be provided with a sensor for collecting medical data indicating one or more measurement parameter to be detected for a patient or a user. One or more software applications may be applied or running for operating the sensor and a data collecting and/or analyzing device operatively connectable to the sensor.

In a process of running a software application so called log data may be collected and stored, for example, in a log data file which is a file that records either events that occur while the software application is running. Logging is the act of keeping a log. Event logs are known as such and record events taking place in the execution of a software application in order to provide an audit trail that can be used to understand the activity of the system and to diagnose problems. Log data entries may be analyzed for different purpose such as error detection.

Document WO 2014/145001 A1 refers to methods and devices for monitoring an analyte in a bodily fluid. In an embodiment the system is configured to manage the storing or logging of information associated with a detected error resulting from the operation of the system. For example, given particular memory or storage unit capacity in the system electronics where certain memory locations are dedicated or assigned for certain types of data, the system may be configured to dynamically manage error logging based on the detected error and the corresponding data bits needed to store the error data bits. For glucose data packet generated corresponding to a sampled glucose level, the system electronics is configured to dynamically allocate least significant bits of the memory locations assigned or set aside for circuit board temperature data to store or log extra or additional error data bits that are not stored in the preset error memory locations in the data storage device. In this manner, all error data bit generated that correspond to each glucose sample is stored in the memory structure of a data storage device or memory unit of the system electronics, by re-allocating some least significant bits of the memory location dedicated for none-error data type.

SUMMARY

It is an object of the present disclosure to provide a method of dynamically saving metadata in a process of operating a medical system and a medical system, thereby, making available reliable and efficient error detection.

According to an aspect, a method of dynamically saving metadata in a process of operating a medical system and a medical system according to the independent claims 1 and 14, respectively, are provided. Further, a computer program product according to claim 15 is provided. Alternative embodiments are disclosed in dependent claims.

According to an aspect, a method of dynamically saving metadata in a process of operating a medical system is provided. The method comprises running a software application for operating a medical device, and storing metadata in a transient memory by a controller, wherein the metadata are assigned to one or more operation events while the software application is running. An error operation event is detected by the controller. In response to the detecting the error operation event, present metadata currently stored in the transient memory and assigned to one or more operation events before the error operation event was detected are transmitted from the transient memory to a log data memory. The present metadata are stored in the log data memory. Further, metadata different from the present metadata and assigned to the error operation event are stored in the log data memory.

According to a further aspect, a medical system is provided, the medical system comprising a medical device, a software application running for operating the medical device, a controller, a transient memory device, and a log data memory. The controller is configured, while the software application is running for operating the medical device, to store metadata in the transient memory, wherein the metadata are assigned to one or more operation events while the software application is running, detect an error operation event by the controller, in response to the detecting the error operation event, transmit present metadata currently stored in the transient memory and assigned to one or more operation events before the error operation event was detected from the transient memory to the log data memory, store the present metadata in the log data memory, and store metadata different from the present metadata and assigned to the error operation event in the log data memory.

According to another aspect, a computer program product is provided, the computer program product preferably stored on a storage medium and configured to perform the method of dynamically saving metadata in a process of operating the medical system.

The medical device may be provided as a single component device or a medical device with a plurality of device components. In an alternative embodiment, the medical device is provided with a sensor configured for sensing medical data for a user or patient. The sensor may be a glucose sensor for detecting sensor data indicative of a glucose level of a patient or user. The sensor may be a glucose sensor for continuous glucose measurement. In an alternative embodiment, the sensor may comprise a sensor to be inserted into the skin of a patient. The sensor may be connected to an analyzing and/or controlling device. During and/or after a measurement sensor signals or sensor data may be transmitted from the sensor to the controlling and/or analyzing device.

The controller detecting the error operation event while the software application is running may be provided with the medical device as an integrated device component. As an alternative, an external controller may be provided separately from the medical device. The external controller may be configured to send signals to and receive signals from the medical device either by wired or wireless connection. Similar alternative embodiments may apply to the transient memory and/or the log data memory.

The controller may be operated by the same software application applied for operating the medical device. As an alternative, another or additional software component may be provided for running the controller.

The medical system may be a continuous glucose monitoring sensor system such as Abbott Freestyle Libre®, Dexcom G5® CGM System, Enlite Glucose Sensors as part of e.g. a MiniMed 640G System, and Roche Accu-Chek Insight CGM and medical devices and controllers contained in such systems.

The log data memory may be a memory having a storage capacity of from about 2 megabyte to about 80 megabyte.

In an alternative embodiment, another software application may be running for operating at least one component of the medical device for providing additional metadata for which steps may be conducted as described for the alternative embodiments.

The metadata may be stored in the transient memory before the error operation event is detected by the controller. There will be metadata stored in the transient memory prior to detecting the error operation event. Therefore, the present metadata to be transmitted to the log data memory in response to detecting the error operation event will comprise metadata stored before the detection of the error operation event. Metadata useful to analyse and explain some reason or root cause of the related error operation event will be available for analysis.

The storing of the metadata in the transient memory may comprise deleting previous metadata assigned to one or more previous operation events while the software application is running. In the process of storing the metadata in the transient memory, earlier or previous metadata assigned to one or more earlier or previous operation events are deleted, thereby, providing data storage capacity for storing new metadata in the transient memory. The deleting may comprise at least one of actively deleting the previous metadata prior to storing the (new) metadata, and overwriting the previous metadata by the new metadata. In the process of deleting all data stored in the transient memory may be deleted.

The transient memory may be operated as a first in first out (FIFO) data buffer for storing metadata. FIFO is a method for organizing and manipulating the data buffer. The oldest (first) data entry is processed first. The FIFO may be implemented as a hardware shift register, or using different memory structures, for example, a circular buffer or list data types An event priority may be assigned to the operation events for which metadata are provided while the software application is running, wherein the event priority is selected from a plurality of different event priorities. The event priorities may indicate different categories of operation events such as critical, warning, information, debug, error, and trace. The event priority may give an indication for which analysis metadata which are assigned a specific event priority are to be analyzed. There may be different kinds of metadata analysis. An analysis of metadata which is assigned a specific event priority may depend on the kind of metadata analysis to be conducted. In an alternative, the event priority assigned to metadata may cause the metadata to be provided to a data analysis tool running in a medical system, for example, for outputting warning signals to the user. For example, metadata assigned to be of a first event priority such as "critical" may be considered being of higher priority than metadata to which a second event priority, such as "information", is assigned. An error priority may be assigned to the error operation event, wherein the error priority is of higher priority than any of the event priorities assigned to the one or more operation events for which the present metadata are stored in the transient memory. An error operation event may be of highest event priority.

The method may comprise determining whether the event priority of the error operation event is of higher priority than the each or any of the event priorities assigned to the one or more operation events for which the present metadata are stored in the transient memory. In this embodiment the relationship between the event priority of the error operation event is to be compared to the event priority of the one or more operation events for which the present metadata are stored in the transient memory. Transmission of the present metadata to the log data memory and storage of the metadata different from the present metadata in the log data memory may be conducted if it is determined that the event priority of the error operation event is of higher priority than each of the event priorities assigned to the one and more operation events for which the present metadata are stored.

An amount of metadata stored in the transient memory while the software application is running may be reaching the maximum data storage capacity of the transient memory. Because the amount of metadata to be stored in the transient memory, while the software application is running, is exceeding the maximum data storage capacity of the transient memory, it will be necessary to delete some of the metadata stored in an earlier stage of the process (e.g. before the error event is detected) in order to provide data storage capacity for metadata collected in a later stage of the process of operating the medical system. If the transient memory is operated as a first in first out (FIFO) data buffer the oldest record (first) data entry is deleted first when the amount of metadata to be stored in the transient memory, while the software application is running, is exceeding the maximum storage capacity of the transient memory. As an alternative, the storage capacity of the transient memory may be sufficient for receiving and storing all metadata to be collected while the software application is running for operating the medical device, for example, during a measurement time period.

The transient memory and the log data memory may be provided in a common memory device. As an alternative, the transient memory and the log data memory may be provided in separated memory devices. The common and the separated memory devices shall be accessible by the controller.

The method may comprise detecting an error operation event selected from the following group of error operation events: failure of a hardware component of the medical device, and failure of a software component of the medical device. For example, there may be failure of one or more of the following hardware components: sensor device, user input device, and output device. With regard to software components, such software components may be provided for running the different hardware components. With regard to software runtime fault, an error operation event may refer to, for example, null pointer exception, calculation overflow, and/or risk mitigation triggered based of unexpected input conditions. Moreover, the error operation event may be due to sensor measurement data (strongly) deviating from sensor measurement data acquired before, e.g. a drop of the calculated glucose concentration by more than about 50% between sensor measurement data acquired within up to about 10 minutes. Other examples may include an error operation event due to sensor data associated with a low signal-to-noise ratio. Also, a battery fault based on temperature may be causing an error operation event.

As used herein, metadata different from the present metadata and assigned to the error operation event can be any metadata that is received by the controller and which metadata is assigned to or associated with a failure of a hardware component of the medical device, and/or failure of a software component of the medical device. Metadata that are generated in relation to the error operation event triggered the fault, in case of software, may refer to code file and/or line number in the software application. With regard to an error operation event related to hardware failure, a hardware identification that triggers the error operation event may be provided.

The method may comprise storing metadata assigned to one or more operation events selected from the following group of operation events: determining an operation parameter related to the operation of the medical device, conducting user interaction with the medical device, determining an operation status of the medical device, and controlling environmental parameters for the medical device. There may be storing of metadata assigned to one or more operation events selected from the following group of operation events: determining an operation parameter related to a functional component of the medical device, conducting user interaction with the functional component of the medical device, determining an operation status of the component of the medical device, and controlling environmental parameters for the component of the medical device.

The metadata may comprise contextual data. The contextual data are assigned to the one or more operation events. The contextual data may refer, for example, to temperature, e.g. body temperature or temperature in the environment of the medical device, air pressure, a user interaction, environmental data, system status information, sensor status information and/or user entry data.

With regard to the medical device, a sensor may be connected to a measurement data collecting and/or analyzing device, such device, for example, being provided as a mobile device like a mobile phone or a wearable device such as smart watch. In the method of dynamically saving metadata in the process of operating a medical device metadata with regard to the operation of the data collecting and/or analyzing device may be provided as it has been described with regard to the metadata above.

The method may comprise, for error analysis, receiving the present metadata, and metadata different from the present metadata from the log data memory, and analysing the present metadata and metadata different from the present metadata read from log data memory. The metadata stored in the log data memory may be analyzed for error analysis. Such data analysis may be processed by the controller and/or some data processing device which is provided with access to the log data memory.

The technologies of the present disclosure may provide for one or more of the following benefits: reducing the energy consumption of the medical system, improving analysis of error operation events detected by the controller, and increasing the types of data that can be stored and used for error analysis when comparing it to previously known methods. Contrary, according to the art, metadata is stored in a large (non-transient) log memory without making use of an "intermediate" transient memory and/or only collected and stored after the error operation event is detected by the controller.

With regard to the medical system, the alternative embodiments described above for the method of dynamically saving metadata in a process of operating the medical system may apply mutatis mutandis.

The medical system may be provided with a portable or non-portable medical device for processing continuous or non-continuous monitoring data indicative of an analyte in a bodily fluid. The medical device may comprise a data interface device which is configured to receive a stream of continuous or non-continuous monitoring data from a body worn sensor, the monitoring data being indicative of an analyte in a bodily fluid. Further, the medical device comprises a storage device which is configured to store the monitoring data at least in part, and a control device which is configured to process the monitoring data and, at least for data exchange, functionally connectable to the data interface device, and the storage device.

According to another aspect, a medical monitoring system is provided, comprising a sensor device to be worn on a body, and a medical device for processing monitoring data indicative of an analyte in a bodily fluid, wherein, for at least unidirectional exchanging data, a data interface of the sensor device and a data interface of the portable device are connectable by a data transmission connection.

In an embodiment, the analyte to be determined may be glucose. Continuous monitoring data indicative of glucose in the bodily fluid may be provided, specifically, blood glucose.

The medical monitoring system may be provided as a continuous glucose monitoring (CGM) system.

The body worn sensor may be a sensor for collecting in vivo sensor data. The body worn sensor may be a continuous monitoring sensor, specifically a continuous glucose monitoring sensor configured to be provided in the interstitium. A sensor session of the body worn sensor may refer to a life cycle or life time of the sensor. The life cycle may be started by connecting the sensor to the portable device for the first tile which may also be referred to as pairing the sensor and the portable device. The life cycle may end at the time of disconnecting the sensor from the portable device.

DESCRIPTION OF FURTHER EMBODIMENTS

Following, embodiments, by way of example, are described with reference to figures. In the figures show:

FIG. 1 a schematic representation of a medical system; and

Figure 2:
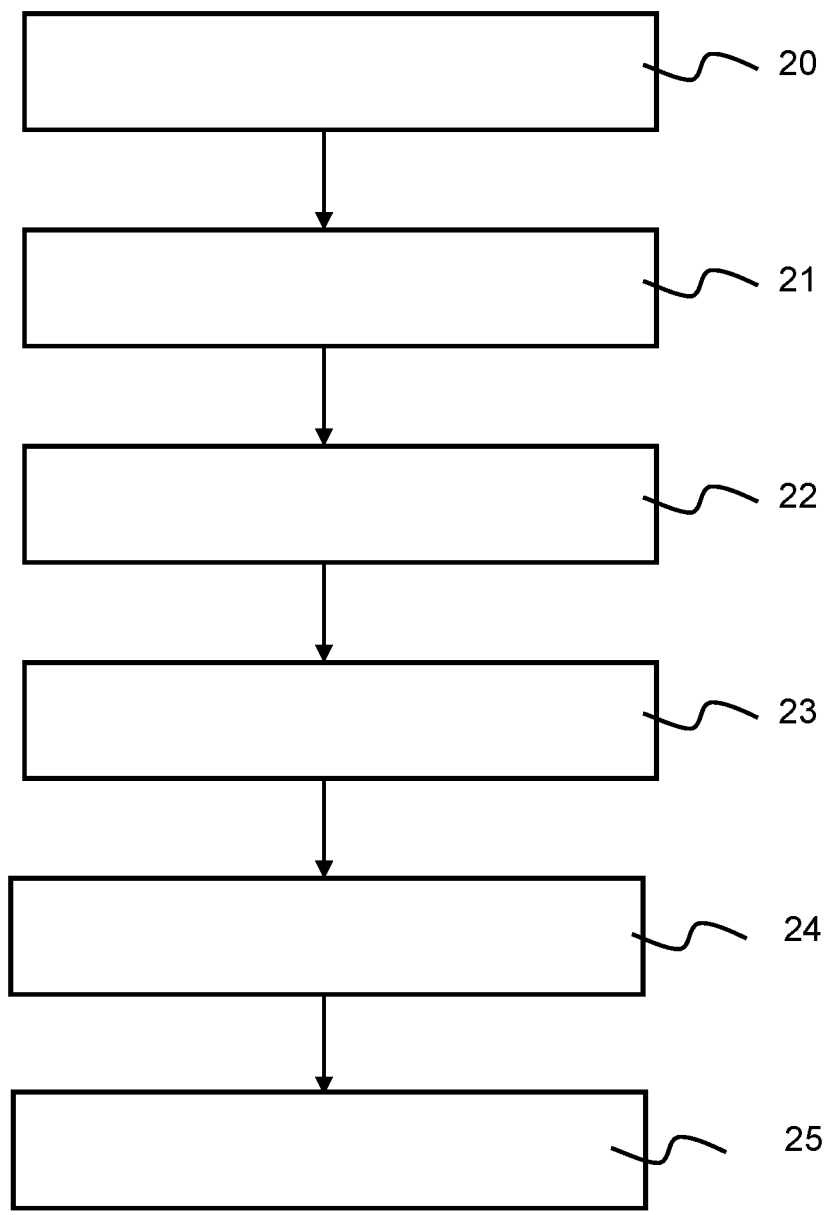

FIG. 2 a schematic representation of a method of dynamically saving metadata in a process of operating a medical system.

FIG. 1 shows a schematic representation of an arrangement or medical system with a medical device 1 and a sensor device 2 provided with a sensor, e.g. a sensor to be worn by a patient. The sensor device 2 is configured for continuous and/non-continuous glucose monitoring. The medical device 1 which may be provided as a portable device is provided with a data interface device 3, a data processing device 4, a storage device 5, and a display device 6. The data processing device 4, at least for unidirectional data transmission, is connected to the data interface device 3, the storage device 5, and the display device 6. Further functional components 7 may be provided.

The data processing device 4 may comprise one or more processors.

Data transmission between the medical device 1 and the sensor device 2 may be provided by wireless and/or wired data transmission. Typically, the medical device 1 receives data from the sensor device 2 via a wireless connection. Preferred interfaces for such wireless communication are operable under Bluetooth or Bluetooth Low Energy Standard. On initiation of the sensor session, the medical device 1 and the sensor device 2 which may be body worn are paired (specifically, exchange of ID information) and during the sensor session the sensor device 2 may constantly transmit raw or preprocessed monitoring data to the medical device 1, where it may be either stored and displayed or only stored and not displayed.

The medical device 1 may be selected from the following group of portable devices: mobile phone, tablet computer, laptop computer, portable medical device, portable medical measurement device, and a smart watch. The portable device may be configured with a software program being downloaded from the internet, for example, in form of one or more so-called Apps.

FIG. 2 shows a schematic representation of a method of dynamically saving metadata in the process of operating a medical device 1.

In step 20, the medical device 1 is provided. For example, the medical device 1 may be configured to determine a blood glucose level for a patient. In the process of operating the medical device 1, one or more software applications are running.

A software application is running for operating the medical device 1 (step 21). With regard to operations or functionalities controlled by the software application, for example, during the operation of the medical device 1, measurement data may be collected by the sensor device 2. Also, in addition or as an alternative, an operation of the medical device 1 may refer to interaction of the medical device 2 with the user, for example, receiving a user input through a user interface.

During the operation of the medical device 1, a plurality of events which are related to the operation of the medical device 1 will take place, such operation events being controlled or overseen by the software application. According to step 22, metadata, for example log data, are provided in the course of the operation of the medical device 1. Such metadata are assigned to the operation events when the medical device 1 is operated. There is a plurality of operation events each assigned metadata, for example, log data. Such metadata provide information related to the operation event to which the data are assigned. In general, the metadata provided during the operation of the medical device 1 may be considered a record indicating a plurality of operation events in the course of operating the medical device 1.

The metadata are stored in a transient memory 5a implemented in the storage device 5 which may be operated as a FIFO. Such operation will ensure that in the transient memory 5a there are always metadata stored related to the latest operation events. Assuming there have been a hundred operation events in the course of the operation of the medical device 1, there will be metadata related to, for example, the latest ten operation events if the data capacity of the transient memory 5a is limited to storing metadata assigned to ten operation events. The transient memory 5a may be a memory having a storage capacity suitable to store metadata collected over a period of time of about 1 s to about 15 s. The transient memory 5a may be a memory having a storage capacity of from about 200 Byte to about 10 kB. For example, a storage capacity may be sufficient for storing metadata related to about twenty operation events.

One or more operation events selected from the following group of operation events may occur while the medical device 1 is operated: determining an operation parameter related to a functional component of the medical device 1, conducting user interaction with the functional component of the medical device 1, determining an operation status of the component of the medical device 1 such as the sensor device 2, and controlling environmental parameters for the component of the medical device 1.

In step 23, an error operation event is detected by a controller implemented by the data processing device 4. In response to the detecting, the metadata presently stored in the transient memory 5a and assigned to one or more operation events before the error operation event was detected are transmitted from the transient memory 5a to a log data memory 5b which, according to the embodiment shown, is also be provided the storage device 5, or, in an alternative embodiment, in a separated storage device.

The error operation event may be selected from the following group of error operation events: failure of a hardware component of the medical device 1, and failure of a software component of the medical device 1. For example, there may be failure of one or more of the following hardware components: sensor device 2, user input device, output device, data interface device 3, data processing device 4, storage device 5, and display device 6. With regard to software components, such software components may be provided for running the different hardware components.

In addition, in step 24, metadata assigned to the error operation event and being different from the metadata sent to the log data memory from the transient memory are stored in the log data memory.

The metadata provided in the log data memory in response to the detecting of the error operation event, in step 25, may be analyzed for detailed error analysis.

In an embodiment, the software application(s) running comprises support code configured to provide documentation of the operation of the medical device 1. For example, it may be recorded that the user has set a threshold value for a parameter, for example, a value of 500 mg/dL. As an alternative or in addition, it may be recorded by the software application running that a functionality A of the medical device 1 was activated by a user input. Metadata related to such operation events are stored in the transient memory 5a. In addition, status information with regard to modules or elements of the medical device 1 may be indicated to a logger such as number of resets, number of tests performed and/or running time (in minutes). Such information data may be stored in a second memory for each category storing only a single event.

If an error operation event is determined, the present metadata from the transient memory 5a are transferred to the log data memory 5b. Such metadata may be written to the log data memory 5b according to the sequence of their detection (storing). Following, the transient memory 5a may be cleared, thereby, deleting at least the present metadata from the transient memory 5a.

If the user provides the medical device 1 for controlling or inspection, for example, providing the medical device 1 to a physician, the log data memory 5b may be read out. For each error operation event happened in the past there is metadata related to the time before the error operation event is happening/detected, such metadata indicating status of the medical device 1 prior to the detection of the error operation event. The metadata from the log data memory 5b may allow for inspection and controlling of the medical device 1.

The invention claimed is:

1. A method of dynamically saving metadata assigned to operation events and metadata assigned to error operation events in a process of operating a medical system, comprising:

running a software application for operating a medical device;

storing operation event metadata in a transient memory by a controller, the operation event metadata being assigned to one or more operation events while the software application is running and before an error operation event is detected, the operation event metadata being stored in transient memory prior to detection of the error operation event, the operation event metadata being assigned to one or more operation events selected from the group consisting of: determining an operation parameter related to an operation of the medical device, conducting user interaction with the medical device, determining an operation status of the medical device, and controlling environmental parameters for the medical device;

detecting the error operation event by the controller, the error operation event being selected from the group consisting of: failure of a hardware component of the medical device, and failure of a software component of the medical device, the error operation event having assigned thereto error operation event metadata different from the operation event metadata;

in response to the detecting the error operation event, transmitting the operation event metadata currently stored in the transient memory from the transient memory to a log data memory;

storing the operation event metadata in the log data memory;

also in response to the detecting the error operation event, transmitting the error operation event metadata to the log data memory; and storing the error operation event metadata in the log data memory.

2. The method according to claim 1, wherein the storing the operation event metadata in the transient memory comprises deleting previous metadata assigned to one or more previous operation events while the software application is running.

3. The method according to claim 1, wherein the transient memory is operated as a first in first out data buffer for storing metadata.

4. The method according to claim 1, further comprising assigning an event priority to the one or more operation events for which operation event metadata are provided while the software application is running, wherein the event priority is selected from a plurality of different event priorities.

5. The method according to claim 4, further comprising assigning an error priority to the error operation event, wherein the error priority is a higher priority than each of the event priorities assigned to the one or more operation events for which operation event metadata are stored in the transient memory.

6. The method according to claim 4, further comprising assigning an error priority to the error operation event, and determining whether the event priority of the error operation event is a higher priority than each of the event priorities assigned to the one or more operation events for which operation event metadata are stored in the transient memory.

7. The method according to claim 1, further comprising an amount of metadata stored in the transient memory while the software application is running exceeding a maximum data storage capacity of the transient memory.

8. The method according to claim 1, further comprising providing the transient memory and the log data memory in a common memory device.

9. The method according to claim 1, further comprising, for error analysis,
receiving the operation event metadata, and metadata different from the operation event metadata from the log data memory; and
analyzing the operation event metadata and the metadata different from the operation event metadata received from the log data memory.

10. A non-transitory storage medium comprising a computer program product, the computer program product configured to perform the method according to claim 1 during operation in a medical system.

11. A medical system, comprising:
a medical device;
a running software application for operating the medical device;
a controller;
a transient memory; and
a log data memory;
wherein the controller is configured, while the software application is running for operating the medical device, to:
store operation event metadata in the transient memory prior to detecting an error operation event, wherein the operation event metadata are assigned to one or more operation events while the software application is running and before the error operation event is detected, the operation event metadata being assigned to one or more operation events selected from the group consisting of: determining an operation parameter related to an operation of the medical device, conducting user interaction with the medical device, determining an operation status of the medical device, and controlling environmental parameters for the medical device;
detect the error operation event, the error operation event being selected from the group consisting of: failure of a hardware component of the medical device, and failure of a software component of the medical device, the error operation event having assigned thereto error operation event metadata different from the operation event metadata; in response to the detecting the error operation event, transmit the operation event metadata currently stored in the transient memory and assigned to one or more operation events before the error operation event was detected from the transient memory to the log data memory; store the operation event metadata in the log data memory; also in response to detecting the error operation event, transmit the error operation event metadata to the log data memory; and store the error operation event metadata in the log data memory.

* * * * *